United States Patent [19]
Graiver et al.

[11] Patent Number: 4,891,388
[45] Date of Patent: Jan. 2, 1990

[54] SOLID GEL DISPENSERS FOR ACHIEVING CONTROLLED RELEASE OF VOLATILE LIQUID MATERIALS AND METHOD FOR PREPARING SAME

[75] Inventors: Daniel Graiver, Midland; Robert E. Kalinowski, Auburn, both of Mich.

[73] Assignee: Dow Corning Corporation, Midland, Mich.

[21] Appl. No.: 366,119

[22] Filed: Jun. 14, 1989

Related U.S. Application Data

[63] Continuation of Ser. No. 309,280, Jan. 26, 1989, abandoned.

[51] Int. Cl.$^4$ ............................................. C08J 9/28
[52] U.S. Cl. ........................................ 521/64; 521/82; 521/88; 521/89; 521/141
[58] Field of Search ................ 521/64, 141, 88, 89, 521/82

[56] References Cited

U.S. PATENT DOCUMENTS

| | | | |
|---|---|---|---|
| 4,094,119 | 6/1978 | Sullivan | 53/400 |
| 4,117,110 | 9/1978 | Horst | 424/76 |
| 4,356,969 | 11/1982 | Obermayer et al. | 523/102 |
| 4,587,129 | 5/1986 | Kliment | 523/100 |
| 4,594,380 | 6/1986 | Chapin et al. | 523/102 |
| 4,663,358 | 5/1987 | Hyon et al. | 521/64 |
| 4,719,040 | 1/1988 | Traas et al. | 512/4 |
| 4,720,409 | 1/1988 | Spector | 428/46 |

FOREIGN PATENT DOCUMENTS

| | | |
|---|---|---|
| 138844 | 5/1985 | European Pat. Off. . |
| 1617995 | 4/1971 | Fed. Rep. of Germany . |
| 2229425 | 1/1975 | France . |
| 2239255 | 4/1975 | France . |
| 2585954 | 2/1987 | France . |
| 147536 | 7/1988 | Japan . |
| 1544221 | 4/1979 | United Kingdom . |

*Primary Examiner*—Morton Foelak
*Attorney, Agent, or Firm*—Robert Spector

[57] ABSTRACT

Aesthetically attractive, free standing dispensers for the controlled release of volatile liquid materials such as perfumes and fragrances into the atmosphere are prepared by (1) forming a first solution by heating a mixture comprising polyvinyl alcohol and water and/or dimethyl sulfoxide under atmospheric pressure, (2) adding a second solution comprising a volatile liquid material and a monohydric alcohol in a solvent that is miscible with the first solution under conditions that avoid precipitation of polyvinyl alcohol, and then (3) cooling the resultant solution to below room temperature to form a gel in the shape of the final dispenser. The exterior surfaces of the dispenser remainds dry to the touch throughout its useful life.

3 Claims, No Drawings

SOLID GEL DISPENSERS FOR ACHIEVING CONTROLLED RELEASE OF VOLATILE LIQUID MATERIALS AND METHOD FOR PREPARING SAME

This is a continuation of co-pending application Ser. No. 309,280, filed on 1/26/89.

BACKGROUND OF THE INVENTION

1. Field of the Invention

This invention relates to the controlled release of volatile materials. More particularly, this invention relates to dispensers for volatile liquid materials such as an air freshener fragrance or a biologically active composition. The dispenser consists essentially of a solid hydrogel containing 90 weight percent of more of a aqueous mixture containing the volatile material, which is dispensed at a uniform, controllable rate into the atmosphere adjacent to the dispenser, while the surface of the dispenser remains dry to the touch throughout the dispensing process.

2. Description of the Prior Art

Dispensers for the controlled release of volatile liquids such as perfumes, deodorants and biologically active compositions are known. One class of dispensers comprise a matrix, such as a film formed from a natural or synthetic organic polymer, that is impregnated with the material to be released. Dispensers of this type are described in U.S. Pat. No. 4,720,409, which issued on Jan. 19, 1988. One major disadvantage of this type of dispenser is the relatively small volume of liquid that can be incorporated into a solid film of an organic polymer without destroying the coherency of the film. This severely limits the useful life of the dispenser.

A second type of controlled release dispenser comprises a reservoir of the volatile liquid material enclosed within either a rigid or flexible container wherein at least a portion of the wall of the container is porous to the volatile liquid. Dispensers of this type are described in U.S. Pat. No. 4,356,969, which issued on Nov. 2, 1982. To reduce the likelihood of leakage of a bulk liquid from the dispenser, the liquid composition containing the volatile materials to be released can be absorbed into a porous material such as a sponge or a polyurethane foam. The impregnated material can optionally be enclosed within a porous container. Dispensers of this type are described in West German Patent No. 1,617,955, which issued on Apr. 22, 1971; French Patent No. 2,585,954, which issued on Feb. 13, 1987; U.S. Pat. No. 4,594,380, which issued on June 10, 1986; U.S. Pat. No. 4,094,119, which issued on June 13, 1978; French Patent No. 2,239,255, which issued on Apr. 4, 1975; and French Patent No. 2,229,425, which issued on Jan. 17, 1975.

In a third type of dispenser the liquid composition containing the material to be released is incorporated into a gel or wax formed from a natural or synthetic organic polymer. Additives to modify the properties of the gel of wax can also be included in the composition.

U.S. Pat. No. 4,117,110, which issued on Sept. 26, 1978, describes an improved solid air deodorant wherein the active ingredient, typically a perfume composition, is combined with paraffin that has been gelled using a metallic soap. The improvements alleged for this product are the presence of the soap, which acts as a support for the hydrocarbon gel, and the ability to select the volatility of the paraffin to achieve an evaporation of both the paraffin and the active ingredient, thereby leaving the external appearance of the dispenser unchanged.

U.S. Pat. No. 4,719,040, which issued on Jan. 12, 1988 teaches absorbing a perfume into a finely divided, water insoluble polymer and combining the resultant mixture with from 0.5 to 10 percent, based on the combined weight of all ingredients, of a gelling agent.

Published European patent application Ser. No. 138,844, which issued on May 2, 1985 teaches achieving continuous diffusion of perfume into the atmosphere by incorporating the perfume composition into a gelling agent such as carrageen or agar containing a mineral substance or fiber such as calcium sulfate, an aluminum silicate or sawdust.

In accordance with the teaching of British patent No. 1,544,221 a volatile material, such as an air freshener fragrance or an insecticide, is combined with a liquid hydrocarbon and a soap of a polyvalent metal, and the resultant composition is incorporated into a spongy gel formed from a lower alcohol and the sodium salt of a higher fatty acid such as stearic acid.

None of the aforementioned prior art gels is completely satisfactory as a dispenser for achieving controlled release of volatile liquids such as perfumes and biologically active compositions.

Two of the most objectionable disadvantages of many prior art gels as dispensers for the controlled release of volatile materials are a wet or otherwise aesthetically unattractive surface and/or the slow rate at which the volatile materials are released from the gel.

When many prior art gels are used to dispense a fragrance or other volatile liquid the gel must be enclosed in a suitable container that conceals the gel and makes it inaccessible to the user of the dispenser, yet allows the volatile liquid to be released into the atmosphere at the desired rate. When the volatile liquid is an air freshener fragrance it is often desirable to have a relatively high initial rate of release, in the order of about 1 gram per hour which then gradually decreases over a period of several hours to a lower rate that is maintained over the useful life of the dispenser.

The preparation of some prior art gels requires blending a number of ingredients in specified proportions to achieve the desired release rate. In other instances the desired release rate cannot be achieved and/or maintained over the entire useable life of the dispenser, or not all of the volatile liquid is capable of being dispensed.

Gels prepared from solutions of polyvinyl alcohol (PVA) in water or a mixture of water and a water-miscible organic solvent such as methanol, propanol, dimethyl sulfoxide and N,Ndimethylformamide are disclosed in numerous patents and other publications. Typical of recently issued patents describing gels formed from aqueous solutions of polyvinyl alcohol is U.S. Pat. No. 4,663,358, which issued to Hyon et al on May 5, 1987. This patent teaches cooling to below room temperature a solution of polyvinyl alcohol in a mixture of water and a water-miscible organic solvent such as alcohols containing from 1 to 4 carbon atoms, glycols and dimethyl sulfoxide. Mixtures of water and dimethyl sulfoxide are preferred, and the water can constitute from 10 to 90 weight percent of the solvent mixture. The gel formed by cooling the solution is then immersed in flowing water to remove the organic solvent. Alternatively the initial gel is dried to remove substantially all of the solvent and then immersed in water to form the hydrogel. This patent also teaches that extraction of the organic solvent may not be necessary for certain end-use applications of the gel, including the controlled release of drugs or perfumes.

The alleged advantage of hydrogels prepared as described in the Hyon patent is their transparency relative to the opaque gels obtained from solutions of polyvinyl alcohol in either water or dimethyl sulfoxide as the only solvent.

The Hyon patent teaches that hydrogels prepared in accordance with the method disclosed in this patent differ from hydrogels prepared at room temperature by the absence of stickiness and improved mechanical strength. The hydrogels are capable of being molded into articles of various shapes, however there is no indication regarding whether the aesthetic properties of the gel other than stickiness differ from those of other prior art gels, specifically, whether any liquid is initially present on the surface of the molded article or exudes to the surface when the article is exposed to the atmosphere for extended periods of time under ambient conditions. If the gel is to be used as a free standing dispenser for the controlled release of a perfume or other volatile material over a period of days or weeks, the presence of liquid materials during this period would be aesthetically unacceptable to the user of such a dispenser.

The present inventors discovered that controlled release dispensers prepared using PVA hydrogel compositions of the type described in the aforementioned Hyon et al. patent are unique with respect to dispensers formed from other hydrogels by virtue of surfaces that remain dry to the touch throughout the useful life of the dispenser. Unlike prior art dispensers, the dispensers of this invention are aesthetically attractive in addition to being free standing, and therefore do not have to be enclosed in a container to conceal the gal and/or prevent leakage of liquid materials that appear on the surface of the dispenser as the volatile material(s) entrapped within the dispenser is released. An advantage of the present dispensers is the ability to mold the gel from which the dispenser is prepared into any desired shape, including Christmas trees, other seasonal articles and various animals.

The present inventors also discovered an improved method for preparing dispensers from solubilizing polyvinyl alcohol that avoids the use of superatmospheric pressure.

SUMMARY OF THE INVENTION

In accordance with this invention aesthetically attractive, free standing dispensers for the controlled release of volatile liquid materials such as perfumes and fragrances into the atmosphere are prepared by (1) forming a first solution by heating a mixture comprising polyvinyl alcohol and water and/or dimethyl sulfoxide under atmospheric pressure, (2) adding to said solution a second miscible solution comprising a volatile liquid material and a monohydric alcohol under conditions that avoid precipitation of polyvinyl alcohol, and then (3) cooling the resultant solution to below room temperature to form a hydrogel in the shape of the final dispenser.

DETAILED DESCRIPTION OF THE INVENTION

This invention provides an improved dispenser for achieving controlled release of a volatile material into the atmosphere, the dispenser comprising a gel formed from at least one organic polymer and a solution of a volatile liquid that is to be released over an extended period of time. The improvement comprises a gel formed by, as a first step, dissolving under atmospheric pressure with heating a polyvinyl alcohol in a solvent comprising water, dimethyl sulfoxide or a mixture thereof to form a first solution, as a second step, adding to said first solution a second miscible solution comprising said volatile liquid and a solvent comprising (a) water or dimethyl sulfoxide and (b) a monohydric alcohol containing form 1 to 8 carbon atoms, where the concentration of polyvinyl alcohol in the final solution does not exceed about 15 percent by weight; and as a third step cooling said final solution to below 25° C. to form a self-supporting gel in the shape of said dispenser, whereby the dispenser is free standing and possesses an exterior surface that is initially dry to the touch and remains so throughout the useful life of said dispenser.

The characterizing features of this invention include (1) using a polyvinyl alcohol (PVA) gel containing no more than about 15 weight percent of PVA, typically less than 10 weight percent, as the matrix material for the dispenser, (2) using as the solvent for the PVA and the volatile liquid a mixture of (a) water or dimethyl sulfoxide or mixtures thereof, and (b) at least one aliphatic monohydric alcohol containing from 1 to about 8 carbon atoms, (3) preparing the solution comprising PVA and the volatile liquid under atmospheric pressure, and (4) obtaining a dispenser that is free standing and remains dry to the touch throughout its useful life.

The Initial Polyvinyl Alcohol Solution

Polyvinyl alcohol is typically prepared by hydrolysis or saponification of polyvinyl acetate. The degree of hydrolysis varies depending upon the intended end use of the polymer. The vinyl alcohol polymers of this invention are preferably fully hydrolyzed and are linear or contain at most a minimal degree of branching. The reason for this preference is to achieve the maximum degree of hydrogen bonding. The formation of hydrogen bonding between hydroxyl groups on adjacent polymer molecules and crystallization of the polymer are considered responsible for the development of the excellent physical properties associated with the cured polymer.

In those instances when hydrogen bonding is not sufficient to achieve the desired properties in the final gel, the PVA can be crosslinked by chemical means, as is well known in the art.

The molecular weight of the polyvinyl alcohol used to prepare the gel and, ultimately, the dispenser is determined by the desired physical and aesthetic properties of the dispenser. The molecular weight of the PVA should not be less than 44,000, preferably not less than 75,000. Commercially available polymers with molecular weights of from 75,000 to 440,000 are preferred for preparing the present dispensers, particularly those polymers containing relatively large concentrations of syndiotactic or isotactic segments within the polymer molecules.

To maximize the concentration of active ingredient, i.e. the fragrance or other volatile liquid, in the dispenser the concentration of PVA in the initial solution should be as low as will allow formation of a gel that retains its integrity and a dry surface in the presence of the solubilized active ingredient. The lower operable concentration limit for the PVA will be at least in part dependent upon the molecular weight of this polymer.

The preferred PVA concentration range will depend upon the molecular weight of the polymer. Typically the properties of PVA gels, particularly tensile strength and elongation at break, increase with increasing concentration and/or molecular weight of the polymer. PVA concentrations of below about 10 weight percent are preferred, although higher concentrations of polymer can be used if it is desired to improve physical properties at the cost of reducing the concentration of liquid ingredients in the final dispenser.

The alcohol portion of the liquid composition used to prepare the present dispenser is a non-solvent for PVA, but is required to solubilize the fragrance or other volatile liquid organic material that is to be released at a controlled rate.

The alcohol constitutes from 10 to 40 weight percent of the solvent, preferably from 20 to 35 weight percent. Alcohol concentrations greater than about 40 weight percent typically result in precipitation of PVA from the solution. This limit may vary depending upon the concentration and molecular weight of the PVA and the temperature of the solution.

The concentration of fragrance or other volatile active ingredient to be released from the present dispensers is typically from about 5 to about 25 weight percent in the solution used to prepare the PVA gel. When the volatile material is a fragrance, a variety of both natural and synthetic floral and herbal fragrances are commercially available and can be used for this purpose.

The first step in the process for preparing a controlled release dispenser of this invention is to dissolve the PVA in water, dimethyl sulfoxide or a mixture of these solvents. A portion of the water/alcohol mixture containing the volatile liquid (the active ingredient) to be released can be added at this time to reduce the viscosity of the PVA solution. Solubilization of the polymer can be facilitated by heating the initial mixture to temperatures from 50° C. up to the boiling point of the mixed solvent and stirring until the polymer is completely dissolved. Heating is preferably done under an atmosphere of nitrogen or other inert gas to minimize degradation of the polyvinyl alcohol.

The fragrance or other active ingredient is preferably dissolved in a mixture of water and an alcohol containing from 1 to 4 carbon atoms. The concentration of alcohol is preferably the minimum required to dissolve the active ingredient.

In accordance with the second step of the present method, when all of the PVA has dissolved, the solution of active ingredient (less any portion previously added) is then added gradually to avoid precipitating the PVA.

Preparation of the Dispenser

The controlled release dispensers of this invention are prepared by cooling the solution containing the PVA and active ingredient. The solution is first poured into a mold cavity corresponding in shape to the dispenser of this invention. The mold containing the solution is then cooled to below 25 degrees C., preferably to at least −10° C., for a period of time sufficient to form a tough gel structure. This time period depends upon a number of variables, including the concentration and molecular weight of the polymer, the rate at which the solution is cooled, and the rate at which the resultant gel is returned to ambient temperature. Taking all of these variables into account, the time period during which the solution is cooled is generally from 2 to 16 hours.

The present inventors found that for the types and concentrations of polymers and the range of processing conditions they evaluated no significant additional improvement in properties of the final dispenser was apparent after 16 hours of cooling.

The advantage of the present method for preparing controlled release dispensers is that the molded gel article obtained by cooling the mixture of PVA, active ingredient and solvents can be used directly as a free standing dispenser for an air freshener fragrance or other volatile liquid. The gel does not have to be confined in a container to avoid leakage of liquid material and/or requiring the ultimate user of the dispenser to handle an exposed wet surface or view an aesthetically unattractive article at any time during the useful life of the dispenser. As disclosed in the preceding specification, the exterior surface of the initial dispenser is dry to the touch and remains dry until the all of the air freshener fragrance or other active ingredient has been released.

It should be apparent that the external dimensions of articles formed from the present air freshener compositions will decrease as the mixture of active ingredient and volatile solvents evaporates into the atmosphere. Under given conditions of temperature and humidity the rate at which the active ingredient is released into the atmosphere will be directly proportional to the external dimensions of the dispenser. The reduction in external dimensions will cease when the supply of active ingredient is exhausted, thereby providing an obvious signal to the user that the useful life of the dispenser is complete. A second method for determining the end of the useful life is to include in the composition used to prepare the dispenser a small amount of a basic or acidic material and a pH indicator such as thymol blue that will undergo a color change within the pH range of from 5 to about 8. The present inventors have found that the indicator will undergo a color change as the concentration of active ingredient approaching zero.

Volatile liquid materials other than perfumes and fragrances that can be released at a controlled rate using the PVA dispensers of this invention include but are not limited to deodorizers and physiologically or biologically active materials such as insect attractants or repellents, pheromones, disinfectants, pesticides, preservatives, and vaporized medications.

The following examples are intended to describe preferred embodiments of the present invention and should not be interpreted as limiting the scope of the invention as defined in the accompanying claims. Unless otherwise specified all parts and percentages specified in the examples are by weight and viscosities were measured at 25 degrees C.

EXAMPLE 1

This example describes the preparation of a preferred type of air freshener dispenser.

A glass reactor was charged with 36 parts each of water and a finely divided polyvinyl alcohol (PVA) exhibiting a molecular weight of 86,000. The mixture was heated with stirring under ambient pressure. When the temperature reached 90° C. 60 parts of a solution of a floral type fragrance in a 65/35 weight ratio water/ethanol mixture was added to the reactor. The resultant mixture was heated at a temperature of 87° C. for about ten minutes until the polymer had completely dissolved, at which time 268 parts of the fragrance solution were added and heating was continued for an additional 20 minutes. An additional 19.38 parts of PVA and 19.4 parts of ethanol were then added to achieve a PVA concentration of 9.0% and a 65/35 weight ratio of water/ethanol in the final solution.

The PVA solution was allowed to cool to 60° C., at which time it was poured into a mold fabricated from silicone rubber. The filled mold was then stored for about 64 hours in the freezer compartment of a residential type refrigerator-freezer that was maintained at a temperature of −20° C. The resultant dispenser of this invention, which was in the shape of a frog (sample 1), was removed from the mold and allowed to remain under ambient conditions while the weight of the dispenser was measured periodically using an analytical balance. The rate of weight loss between each of the weight measurements was calculated and appears in Table 1. The dispenser remained dry to the touch throughout the entire testing period.

For purposes of comparison the rate of weight loss exhibited by a commercially available wick type air freshener dispenser was determined and these data appear in Table 1 under the heading "Comparative Sample".

The dimensions of sample 1 were 8.63 cm. long at its longest point, 6.12 cm. wide at its widest point and 4.67 cm. high at its highest point. As the liquid evaporated and the fragrance was released over a period of 30 days the dispenser shrank to final dimensions of 4.88 cm. maximum length, 3.43 cm. maximum width and 2.73 maximum height.

The weight of the dispenser reached a constant value after about 30 days, indicating that all of the available fragrance had been released.

TABLE 1

| Sample 1 | | Comparative Sample | |
|---|---|---|---|
| Time (Hrs.) | Weight Loss Rate (Grams/Hour) | Time (Hrs.) | Weight Loss Rate (Grams/Hour) |
| 0.00 | 0.00 | 0.00 | 0.00 |
| 0.08 | 0.59 | 1.00 | 0.52 |
| 0.30 | 0.78 | 2.00 | 0.435 |
| 0.53 | 0.95 | 3.50 | 0.371 |
| 1.03 | 1.18 | 17.8 | 0.283 |
| 1.45 | 1.30 | 19.3 | 0.278 |
| 1.85 | 1.36 | 21.5 | 0.276 |
| 2.10 | 1.40 | 23.3 | 0.274 |
| 3.22 | 1.45 | 25.0 | 0.272 |
| 4.15 | 1.45 | 41.8 | 0.247 |
| 4.48 | 1.45 | 47.3 | 0.24 |
| 5.08 | 1.44 | 49.3 | 0.24 |
| 5.71 | 1.42 | 66.0 | 0.22 |
| 6.38 | 1.40 | 69.5 | 0.22 |
| 22.5 | 0.98 | 73.0 | 0.21 |
| 30.0 | 0.90 | 137.8 | 0.17 |
| 70.29 | 0.61 | 241.5 | 0.13 |
| 100.0 | 0.48 | 329.8 | 0.11 |
| 148.9 | 0.36 | 402.8 | 0.10 |
| 247.7 | 0.25 | 474.3 | 0.09 |
| 338.1 | 0.19 | 578.1 | 0.08 |
| 406.3 | 0.16 | 641.8 | 0.08 |
| 435.6 | 0.15 | 720.5 | 0.07 |
| 550.3 | 0.12 | | |
| 602.2 | 0.11 | | |
| 679.7 | 0.10 | | |
| 698.8 | 0.10 | | |

It is evident from the data in Table 1 that while the useful lives of both dispensers are equivalent, the dispenser of this invention (sample 1) is unique in its ability to provide a relatively rapid initial release rate (1–1.5 grams per hour) during a period beginning after about the first 30 minutes and lasting for about 22 hours, after which the rate begins to gradually decrease for the remainder of the useful life of the dispenser. The release rate of the comparative example decreases from an initial rate of 0.5 gram per hour to 0.3 gram per hour over a period of about 18 hours, after which it gradually decreases to 0.1 gram per hour over the remaining life of the dispenser.

EXAMPLE 2

This example demonstrates that a solution of polyvinyl alcohol in a water/ethanol mixture containing a solubilized volatile ingredient cannot be prepared under ambient pressure using conventional heating means. The general method taught in the aforementioned U.S. Pat. No. 4,663,358 to Hyon and Ikada requires heating mixtures of PVA, water and a water-miscible organic liquid in an autoclave or using a high frequency heater to generate the heat required to solubilize the polymer.

A glass reactor was charged with 10 parts of PVA having a number average molecular weight of 86,000 and 90 grams of a solution of a floral type fragrance in a 65/35 weight ratio water/ethanol mixture. The contents of the reactor were stirred and heated to the boiling point (82° C.) using a conventional electrically powered heater. After 30 minutes of heating a substantial quantity of PVA remaining undissolved.

That which is claimed is:

1. In a method for preparing a dispenser for achieving controlled release of a volatile liquid into the atmosphere, the method consisting essentially forming by heating a solution comprising polyvinyl alcohol, said volatile liquid and a solvent for both the polyvinyl alcohol and the volatile liquid, and then cooling sid solution to form a gel in the shape of said dispenser, the improvement consisting essentially of A. dissolving under atmospheric pressure with heating a polyvinyl alcohol in a solvent comprising water, dimethyl sulfoxide or a mixture thereof to form a first solution, B. as a second step, adding to said first solution a second miscible solution comprising said volatile liquid and a solvent comprising (a) water or dimethyl sulfoxide and (b) a monohydric alcohol containing from 1 to 8 carbon atoms, where the concentration of polyvinyl alcohol in the final solution does not exceed about 15 percent by weight;

C. obtaining a self-supporting gel in the shape of said dispenser, where said gel is free standing and possesses an exterior surface that is initially dry to the touch and remains so throughout the useful life of said dispenser.

2. A method according to claim 1 where said volatile liquid is a fragrance, disinfectant or a biologically active material, the solvent for said final solution is a mixture of water and an alcohol, where said alcohol constitutes less than 40 weight percent of said solvent, the molecular weight of the polyvinyl alcohol is from 75,000 to 440,000, said first solution is prepared by heating a mixture of solid polyvinyl alcohol and a solvent comprising water to a temperature of at least 50° C. said final solution is cooled to a temperature of at least −10° C. to form said gel, and said dispenser contains an acidic or basic material and a pH indicator that underges a color change within the pH range of from 5 to about 8 as a means for signaling the end of the useful life of said dispenser.

3. A method according to claim 2 where the volatile liquid is an air freshener fragrance and is present at a concentration of from 5 to 25 weight percent, based on the weight of the solvent in said final solution, said alcohol is ethanol and is present at a concentration of from 20 to 35 weight percent, based on the weight of the solvent present in said final solution.

* * * * *